(12) United States Patent
Dau et al.

(10) Patent No.: US 11,344,257 B2
(45) Date of Patent: May 31, 2022

(54) ELECTRONIC CONTAINMENT SYSTEM FOR STORING AND CHARGING AN INSTRUMENTED INTRA-ORAL APPLIANCE, AND TRANSMITTING DATA THEREFROM

(71) Applicant: Biomechanics Consulting and Research, LLC, Charlottesville, VA (US)

(72) Inventors: Nathan Dau, Palmyra, VA (US); Jeff Crandall, Charlottesville, VA (US)

(73) Assignee: BIOCORE LLC, Charlottesville, VA (US)

( * ) Notice: Subject to any disclaimer, the term of this patent is extended or adjusted under 35 U.S.C. 154(b) by 731 days.

(21) Appl. No.: 16/158,778

(22) Filed: Oct. 12, 2018

(65) Prior Publication Data

US 2019/0110746 A1   Apr. 18, 2019

Related U.S. Application Data

(60) Provisional application No. 62/571,410, filed on Oct. 12, 2017.

(51) Int. Cl.
*A61B 5/00* (2006.01)
*A61B 5/145* (2006.01)
(Continued)

(52) U.S. Cl.
CPC ............ *A61B 5/682* (2013.01); *A61B 5/0022* (2013.01); *A61B 5/02055* (2013.01); *A61B 5/02438* (2013.01); *A61B 5/14542* (2013.01); *A61B 5/746* (2013.01); *A61F 5/566* (2013.01); *A61L 2/10* (2013.01); *A63B 71/085* (2013.01); *A61B 2560/0214* (2013.01); *A61B 2560/06* (2013.01); *A61B 2562/0219* (2013.01); *A61B 2562/24* (2013.01); *A61B 2562/242* (2013.01); *A61C 7/08* (2013.01); *A61C 19/02* (2013.01);
(Continued)

(58) Field of Classification Search
None
See application file for complete search history.

(56) References Cited

U.S. PATENT DOCUMENTS

6,417,761 B1 * 7/2002 Elliott ..................... A61C 7/00
128/859
9,980,799 B2 * 5/2018 Wilson ..................... A61C 7/08
(Continued)

*Primary Examiner* — Shirley X Jian
(74) *Attorney, Agent, or Firm* — Woods Rogers PLC; Nathan A. Evans (57) ABSTRACT

The present invention is a holding case for an instrumented intra-oral appliance containing recorded data, which charges the intra-oral appliance while not in use and transmits recorded data to storage for review and analysis. The transferred data may be subjected to downloading, validation, storage, analysis, measuring, database fusion (with for example data from other devices), data output, and data recording. Output may be further transferred to a computer, processor, phone, tablet computer, or other hardware for review by a user or technical, research, medical, or other oversight personnel. The holding case can also send data to the appliance including firmware or other onboard operating instructions. The holding case can include additional features such as custom dentition of the user, UV light, or a visual user interface.

26 Claims, 4 Drawing Sheets

An electronic "smart" case with a battery (1010), electronics including memory and a microprocessor (1020), and the geometry of the wearer's dentition fit into the bottom half of a case (1030). The instrumented mouthguard (1040) is also shown.

(51) Int. Cl.
*A61B 5/024* (2006.01)
*A63B 71/08* (2006.01)
*A61F 5/56* (2006.01)
*A61L 2/10* (2006.01)
*A61B 5/0205* (2006.01)
*A61C 7/08* (2006.01)
*A61C 19/04* (2006.01)
*A61C 19/02* (2006.01)

(52) U.S. Cl.
CPC ........... *A61C 19/04* (2013.01); *A61L 2202/24* (2013.01); *A63B 2230/06* (2013.01); *A63B 2230/20* (2013.01)

(56) References Cited

U.S. PATENT DOCUMENTS

| | | | | |
|---|---|---|---|---|
| 10,470,847 B2* | 11/2019 | Shanjani | ............... | H04B 5/0056 |
| 10,588,728 B2* | 3/2020 | Wilson | ................ | B65D 43/163 |
| 10,772,714 B1* | 9/2020 | Chapman | ............... | H04W 4/029 |
| 10,888,396 B2* | 1/2021 | Shanjani | ................ | A61C 7/002 |
| 2007/0277836 A1* | 12/2007 | Longley | .................. | A61F 5/566 |
| | | | | 128/848 |
| 2009/0323370 A1* | 12/2009 | Koo | ..................... | A61B 1/0676 |
| | | | | 362/573 |
| 2012/0172677 A1* | 7/2012 | Logan | ................ | A63B 21/0054 |
| | | | | 600/301 |
| 2014/0134561 A1* | 5/2014 | Smith | ................... | A61B 5/1468 |
| | | | | 433/6 |
| 2015/0190537 A1* | 7/2015 | Kerr | ..................... | B08B 7/0057 |
| | | | | 134/1 |
| 2016/0100924 A1* | 4/2016 | Wilson | .................... | H02J 50/10 |
| | | | | 206/63.5 |
| 2017/0086760 A1* | 3/2017 | Kim | ...................... | A61B 6/145 |
| 2017/0165041 A1* | 6/2017 | Wilson | ............... | G06K 9/00805 |
| 2018/0000563 A1* | 1/2018 | Shanjani | ................ | A61B 5/682 |
| 2018/0184795 A1* | 7/2018 | Pai | ........................ | A61C 17/224 |
| 2020/0093571 A1* | 3/2020 | Shanjani | ................. | H04Q 9/00 |

* cited by examiner

Figure 1: An electronic "smart" case with a battery (1010), electronics including memory and a microprocessor (1020), and the geometry of the wearer's dentition fit into the bottom half of a case (1030). The instrumented mouthguard (1040) is also shown.

Figure 2: A hollow model of a wearer's dentition from the occlusal surface (2010) and the underside (2020), depicting an inductive coil to charge the intra-oral appliance.

Figure 3: A standard case with electronics in one end depicted in yellow (3010) and a portion of the wearer's dentition with an intra-oral appliance (3020) depicting the three degrees of freedom (3030) used to align the inductive coil in the case with inductive coil in the intra-oral appliance.

Figure 4

ELECTRONIC CONTAINMENT SYSTEM FOR STORING AND CHARGING AN INSTRUMENTED INTRA-ORAL APPLIANCE, AND TRANSMITTING DATA THEREFROM

CROSS-REFERENCE TO RELATED APPLICATION

The present application relies on the disclosures of and claims priority to and the benefit of the filing date of U.S. Provisional Application No. 62/571,410, filed Oct. 12, 2017. The disclosures of that application are hereby incorporated by reference herein in their entireties.

BACKGROUND

Field of the Invention

The present invention is directed to a holding case for an instrumented intra-oral appliance containing recorded data, which charges the intra-oral appliance while not in use and transmits recorded data to storage and/or for processing. The transferred data may be subjected to downloading, validation, storage, analysis, measuring, database fusion (with for example data from other devices), data output, and data recording. Output may be transferred to a cloud server, computer, processor, phone, or other hardware for review by a user.

In one aspect, the case includes a portion of the intra-oral appliance wearer's 3D dental geometry, which matches or mirrors the particular custom-shaped intra-oral appliance's geometry. In another aspect, the invention comprises an apparatus for performing an intra-oral appliance integrity check within the holding case. In a preferred embodiment of the present invention, the case includes a mechanism for transferring of data from the case and/or intra-oral appliance to a cloud server or other physical or virtual storage media where the data can be processed, reviewed, and/or analyzed by the appliance wearer and/or technical, research, medical, or other oversight personnel. In a related aspect, the data is transferred from the case and/or intra-oral appliance to a central data hub such as a computer, processor, phone, server, or storage unit, which then transmits the data to a cloud server or other storage medium where the data can be reviewed by the appliance wearer and/or, technical, research, medical, or other oversight personnel. In an aspect of this embodiment, the data may be processed or analyzed before or after it is reviewed.

In another embodiment, the case includes a UV light source within, near, or affixed to the holding case to completely or partially sterilize the intra-oral appliance.

In one embodiment, the case has a visual and/or graphical user interface such as a touchscreen, a series of LEDs or a single LED, a series of multicolor LEDs or single multicolor LED, and/or physical buttons or switches.

In another embodiment, a system of holding cases matched with instrumented intra-oral appliances containing recorded data, charges the intra-oral appliances while not in use and transmits recorded data from each individual appliance labeled by appliance or appliance user to a storage and/or processing device, such as an internal or remote storage and/or processing device, for review, processing, and/or analysis.

In yet another embodiment, the case includes a mechanism to identify its unique intra-oral appliance when in proximity to the case using a wireless protocol such as radio frequency identification (RFID), near field communication (NFC), Bluetooth low energy (BTLE), or other low energy communication protocol.

DESCRIPTION OF THE RELATED ART

All references disclosed herein are incorporated by reference.

U.S. Pat. No. 3,938,018 describes a device that charges a DC battery without physical connection between the charger and the battery.

U.S. Pat. No. 4,873,677 describes a device that includes inductive coils to charge a DC battery including a mechanical yoke in the charger case that aligns the inductive coils. In aspects, the current invention uses the wearer's anatomy as the alignment between the appliance and the charging case.

U.S. Patent Application Publication No. 2016/0250517 describes a system for monitoring a team sport activity including a plurality of training devices and a singular docking station to transfer data from the plurality of training devices to the singular docking station and charge the numerous training devices. The system teaches sending data within service broadcasting packets. The current invention embodies a unique, custom case for one specific intra-oral appliance that is associated with the case, whereby the case not only charges the matched appliance, but also, in some aspects, transmits data recorded on the appliance, sanitizes the device, etc. One case per appliance eliminates the need of the system administrator to handle individual devices which are exposed to and possibly covered in the wearer's bodily fluids, such as saliva or sweat. The addition of individual cases for each appliance reduces the risk of contamination of the wearer's device by third party handling, cross contamination by the handling of multiple devices, or contamination of the system administrator.

U.S. Pat. No. 8,092,251 describes an active packaging for electronic media device which provides power to the device while in packaging. The intent of the current invention is to charge the appliance for continued use and download the data from the appliance. These increase the functionality of the appliance by limiting the interaction with individual devices and increases the time between charges.

U.S. Patent Application Publication No. 2015/0097700 describes a plurality of athlete monitoring systems which connect to a plurality of docking stations for charging. However, the current invention stores data on the monitoring/measurement device, while the teachings of Application No. 2015/0097700 describe streaming data live to a base station. The invention described herein allows for both individual charging and data transmission from the plurality of appliances to a unique matched case.

SUMMARY

The present invention is a holding case for an instrumented intra-oral appliance containing recorded data. The holding case downloads data for transfer to, in one embodiment, a central data location and charges the instrumented intra-oral appliance, among other things. The holding case may also include 3D dental geometry of the wearer to receive the appliance and can perform additional tasks such as a device integrity check, sterilization, and provide a visual user interface for the user. The invention includes the implementation of a single holding case or a group of holding cases as part of a system of cases to monitor a specific population.

In a preferred embodiment, the present invention is a holding case for an instrumented intra-oral appliance containing recorded data. The holding case transfers data bilaterally with the appliance allowing for the data from the appliance to be processed, analyzed, validated, compiled, and/or stored on the case or in another location, and data, input, information, instructions, or commands can be sent to the case to modify the operation of the appliance. The case may also include a processor to process information from the appliance. The case may also include a storage medium to store information from the appliance. The case may also include an antenna to send information from the appliance, before or after processing, to a remote electronic device, such as a server, computer, processor, phone, or television, by way of example.

In another embodiment, the case may comprise the apparatus for holding the intra-oral appliance, electronics for charging the electronic intra-oral appliance, electronics for downloading and/or transferring data, and in some aspects custom dentition. The electronics may be glued, potted, snap-fitted, adhered, taped, press-fitted, or otherwise attached to the case. The custom dentition may be 3D-printed, thermoformed, pressure formed, injection molded or otherwise manufactured. The custom dentition may be glued, snap-fitted, pressure fitted, adhered, sonic welded, or otherwise attached to the case and/or electronics.

In one aspect, the holding case includes 3D dental geometry of the wearer to receive the appliance. This would facilitate the accurate placement of inductive coils and radio antennae for charging and data transfer. Accurate receipt of the appliance, as defined by a field detect in the inductive coil of the case, may also initiate reading of data, transfer of data, charging, integrity checks, or other functions performed by the case.

The holding case, in some aspects, performs additional tasks, such as device and data integrity checks. These tasks are performed using sensors on or in the appliance, and/or unique sensors within, in, or on the holding case, or using a processor within, near, or on the appliance that, in aspects, may have superior computing power to that contained within the appliance, or may be the same processor. Alternatively, a processor in, on, or near the holding container/case may be used.

In another aspect, a device integrity check includes the measurement of frequency data measured by sensors in the appliance when the appliance is inserted into the case. The action of inserting the device into the case, in aspects, initiates data recording on the appliance, which also initiates the appliance or the appliance case performing an integrity check on the data. In other cases, a user may manually control when data is sent or received, or integrity checks performed.

A device integrity check may include sensors in the appliance case to measure interaction between the appliance and the 3D dental geometry in the case including, but not limited to, surface area, force, pressure, or strain. Changes in surface contact would indicate the appliance has been mechanically deformed.

In one aspect of this invention, the case comprises a UV light source within the holding case that sterilizes the intra-oral appliance. The UV light source is designed to irradiate most or all surfaces of the appliance for sufficient duration to sterilize the appliance and is timed to occur before, during or after transmission of data.

The holding case, in certain aspects, includes a visual user interface. The visual user interface provides the user information regarding the appliance including that the correct appliance is in proximity to the case, that the appliance needs to be serviced or replaced, that the appliance is not properly placed in the case, or the status of its data download, the status of the charge, that data should be reviewed by the user on another device, that the user should contact technical, research, medical, or other oversight personnel, and other functions relating to the appliance, the user, and/or data on the appliance. The visual user interface may be provided on a separate device such as a tablet, smartphone, computer, server, or other electronics display.

In another embodiment, the visual user interface provides a third party such as a parent, coach, practitioner, or technical, research, medical, or other oversight personnel, information regarding the case and/or the appliance, including if it needs to be serviced or replaced, the status of its data download, the status of the charge, the amount of time the appliance has been in use, if the device memory is full, that data should be reviewed on another device, etc. Such visual user interface provided to a third party may also act as an alert of the state of the user or the appliance, for example a visual indicator may be provided to communicate a traumatic head impact event experienced by the person wearing the appliance.

The invention comprises the implementation of a single holding case or a group of holding cases which are part of a system to record and transmit data related to a specific population. An implementation of a group of holding cases as a system, in one aspect, also includes a central hub that charges the holding cases or stores, analyzes, or processes information. The charging of the cases could be accomplished either wired or wirelessly.

In one embodiment, firmware updates for cases or appliances are transferred from the central hub, a server, or a computer to the cases and/or appliances, or a singular case and/or appliance. This file transfer can be performed over the air via wireless protocol, through an inductive coil used for charging and transferring data, through a direct wired connection, or any other means.

Such firmware updates may be for the appliances, in which case the firmware would be transferred from the central hub, a computer, or a server directly to the appliances, or through the case as connected to the appliance. This file transfer can be performed over the air via wireless protocol, through an inductive coil used for charging and transferring data, through a direct wired connection, or any other means.

In another aspect, data from an appliance or a plurality of appliances are reviewed on a local central storage device. The local storage device may include, but is not limited to, a phone, tablet, computer or other electronic device with a user display.

In yet another aspect of this invention, the data from an appliance or a plurality of appliances are reviewed remotely after data has been sent to a cloud server location, another computer, a phone, or other remote electronic device. The data can be reviewed as a whole, or a subset of data can be reviewed that is selected manually, randomly, based on specific criteria, or based on data integrity evaluations conducted by the appliance, the appliance case, the central data hub, computer software, or cloud-based software.

In one embodiment, the only data observed from an appliance or a plurality of appliances locally is their charge and download status to protect the data privacy of the appliance's wearer from the local system administrator.

In one embodiment of the present invention, a case for an electronic intra-oral appliance is provided that charges the intra-oral appliance, and downloads and/or transfers data from the intra-oral appliance. Charging may be accomplished by wired or wireless means of providing electricity to the case and/or the intra-oral appliance coupled to the case.

In another embodiment of the present invention, the case transfers data to a computer, smartphone, tablet computer, processor, a server, or the cloud for storage and analysis. Such analysis may include, but is not limited to, human performance data or health metrics, blood oxygen level, heart rate, head kinematics (e.g., experienced during impact events, with an emphasis on avoiding recording false positives), etc.

In another embodiment, data transferred from the intra-oral appliance and the results of the analysis are sent for review by a user, such as on a computer, television, smartphone, tablet, or other hardware. The analysis of the data may occur on a processor, a computer, a smartphone, a tablet, or any other software located on hardware, a server, on the cloud, or otherwise. The data may be transmitted to a central repository either wirelessly or by wired communication/connection. In other embodiments, the analysis and output may be performed by electronics and/or processor(s) located on, in, or near the case. Data may also be stored on a storage device on, in, or near the case.

In another embodiment, the data analysis feedback to a user may comprise biostatistics, indication of possible traumatic event, injury, or condition, possible diagnoses of a traumatic event, injury, or condition, along with possible treatment of such event, injury, or condition, including whether to consult with a physician.

In another embodiment, the data analysis feedback to technical, research, medical, or other oversight personnel may comprise biostatistics, indication of possible traumatic event, injury, or condition, possible diagnoses of a traumatic event, injury, or condition, along with possible treatment of such event, injury, or condition, including whether to consult with a physician.

In another embodiment, the data analysis feedback to technical, research, medical or other oversight personnel may comprise biostatistics, indication of elevated risk of possible traumatic event, injury, or condition, or possible prescriptive treatments or alterations in training to mitigate the elevated risk of possible traumatic event, injury, or condition.

In another embodiment, the case and associated software/firmware may perform electronics, structural, data, and other integrity checks on the intra-oral appliance. Feedback is provided to a user if, for example, the electronics, structure, data, or other component of the intra-oral appliance and/or recording system has been compromised. In the case of a group of cases as part of a system, feedback is provided to the system administrator.

In another embodiment, the results of electronics, structural, and data integrity checks are sent to research, technical, medical, or other oversight personnel. If the device requires replacement or service, notification is sent for a replacement appliance to be manufactured or shipped to replace the damaged or compromised device.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

DETAILED DESCRIPTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entireties.

Embodiments of the invention also include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e. processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g. software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In embodiments, the case and associated electronics are designed such that a single design can accommodate a wide range of custom or non-custom intra-oral appliances. In aspects, the electronics components and/or electronic circuitry are located toward one end of the case with an inductive coil facing the remaining open section of the case. A portion of the wearer's dentition is, in aspects, the only unique part of the case. The rest of the case may be standard. In aspects, a coil in the appliance is aligned with an inductive coil in the case. The portion of the wearer's dentition can be moved in two linear axes and a rotational axis in the plane of the two linear axes within the case and the bottom surface can be modified to align the coils in the vertical axis and around the other two rotational axes.

In such an example, the case is capable of communicating via one or multiple communication protocols. The case may communicate with the intra-oral appliance via a low power communication protocol such as Bluetooth low energy or even by physical connection between the appliance and case, and data from the appliance may be communicated to a central data hub, computer, server, or other electronic device via WIFI, wired communication, or any other communication protocol. Data from the appliance may also be communicated to a processing unit in, on, or near the case, which may then be processed on the case and, in aspects, information from this processor may be sent to the intra-oral appliance; alternatively, this data, either pre-processed or not processed may be communicated to a remote electronic device. Data from the appliance may also be communicated to storage media located in, on, or near the case. This stored data may be processed directly in, on, or near the case, or sent to a remote electronic device, such as a server, computer, phone, or television for processing. Accordingly, data from the appliance may be sent directly from the appliance to a remote electronic device, including storage and/or processing unit; data from the appliance may be sent to a processor in, on, or near the case; and/or data may from the appliance may be sent to storage media in, on, or near the case. These various options allow all communication which may occur between the appliance and the case to occur within the case, or outside remote electronic devices may be used to assist with data transfer, processing, storage, analysis, or other use of the data from the appliance and/or the case.

A case or a plurality of cases may be part of a system of cases. The cases may powered externally by a central power source or by battery (internal or external). Each case, when powered, downloads data from its paired appliance via Bluetooth low energy, for example, and charges the paired device via an inductive coil, in certain aspects. The case uploads the data to a processer, a server, or a cloud based server via WIFI, wired communication, or any other communication protocol. After the case or cases have completed downloading and uploading the data from the appliances to a central data hub, for example, they can remain connected to the central power source or each individual case can be powered individually to enable the complete charging of the appliance.

In the example in which cases are part of a system of cases, the cases may be powered by an external or internal power source. Each case, when powered, downloads data from its paired appliance via Bluetooth low energy, for example, and charges the paired device via an inductive coil, a battery, or wired power source. The case uploads the data to a cloud-based server, a processor, a storage unit, a controller, a computer, a phone, a server, or any remote electronic device via WIFI or any other communication protocol. After the case or cases have completed downloading and uploading the data from the appliances to a central data hub, for example, they can remain connected to the external power source to complete the charging of the appliance.

In preferred embodiments, the present invention is directed to a holding case/container for an instrumented/electronic intra-oral appliance containing recorded data, which charges the intra-oral appliance while not in use and transmits recorded data to storage or processing for review and analysis; storage or processing can be in, on, or near the container, or remote from the container. In aspects, after the stored data is analyzed or otherwise processed, information can be transmitted back to the case and/or appliance. Including these features in the appliance's case increases the utility of the appliance itself. A larger capacity battery can be placed into a case than can be placed within the appliance itself, or other power can be applied to the appliance. This enables charging during typical storage of the appliance. Also, because of the battery or other power source, the frequency of charging the case is reduced, which would limit the number of times a user needs to plug-in or place the case on an inductive charging pad, for example. By having the case automatically transfer data from the appliance to the case, a processor, a controller, a computer, a phone, a server, the cloud, and/or a remote electronic device, the user is not burdened with this process, and greater computing power may be used in electronics not having to be located in the appliance itself. This is especially beneficial if data does not need to be reviewed immediately, such as if it is to be stored, reviewed, and/or analyzed at a later time.

In one embodiment, the case will further be able to transfer data downloaded from the appliance to a secondary device. This allows for the utilization of existing user interfaces and computing power in devices such as computers, processors, controllers, computer processing units, laptops, smartphones, servers, etc. This also allows data and software from other sources, such as from remote electronic devices, to be combined and connected to the case and/or the appliance, and analysis, processing, and/or storage to be performed on a larger set of data with enhanced software and/or computing power.

In another embodiment, a portion of the wearer's 3D dental geometry is integrated into the case. In one aspect, this allows for the alignment of inductive charging coils with a battery or batteries, or a mating coil or coils, associated with the appliance. In small devices such as an instrumented intra-oral appliance, the inductive coil is small and susceptible to misalignment with its mating coil. This misalignment causes reductions in the charging efficiency and results in heating of the coil. By using the wearer's 3D dental geometry to design the appliance and the case, the inductive coils can be aligned. Further, the mechanical retention designed to hold the appliance in place on the wearer's dentition also acts to hold the appliance in the correct position in the case.

Including a portion of the wearer's 3D dental geometry also facilitates including mechanical integrity tests into the case. Wearers often chew on their intra-oral appliance. In some cases, pets will chew on appliances. This can cause accelerated wear of an intra-oral appliance and can diminish or eliminate the proper fit of the appliance. If an appliance does not fit correctly, it could collect erroneous data. An ill-fitting appliance could also have diminished effectiveness in applying forces to teeth in the case of orthodontic appliances. Having a representative portion of the wearer's 3D geometry in the case allows for checking the mechanical integrity, shape, and/or alignment of the appliance. In one aspect, the mechanical integrity test is passive within the case. For example, if the appliance has an inertial sensor such as an accelerometer, the act of seating the appliance onto the dentition in the case would generate acceleration data on the appliance. The appliance could record that signal or event of seating into the case. When the case downloads the data, it could evaluate the last event to determine if it has the expected features including frequency content, magnitude, duration, etc.

In another aspect, the mechanical integrity test is active by, for example, including additional sensors in the appliance case. Specific contact points or areas of the wearer's dentition that are critical to retention could be instrumented in the case. Those areas could have load cells, force sensors, strain gauges, pressure sensors, or some other type of sensor located either on the dentition or integrated into the dentition to measure the mechanical fit of the appliance. A predetermined threshold of force, strain, and/or pressure could be used to evaluate if the mechanical properties of the device have changed.

The results of an active or passive mechanical integrity check are then communicated to either the wearer or technical, research, medical, or other oversight personnel. The user is informed if he/she is in charge of managing the device and ordering a replacement. In other cases, the parents, coach, practitioner, or other third party would be notified if a user's device needed to be replaced (for example, if the user is a child). Other scenarios exist in which the negative results of a mechanical integrity test could be sent to the wearer's doctor, dentist, orthodontist, etc., which would facilitate the generation of a prescription for a replacement. For example, in the case of non-prescription appliances, the negative results of a mechanical integrity test could be provided to a team equipment manager, sports scientist, or the device manufacturer to enable the most expeditious replacement or correction of the device.

Including a portion of the wearer's 3D dental geometry also facilitates transfer of data. If the dental geometry of the appliance and the 3D geometry in the case line up or otherwise match, it may signal and initiate the transfer and/or receipt of data.

Since, in embodiments, the case facilitates the transfer of data to a processor or another device for the evaluation and analysis of data, this provides broad implementations where both the appliance wearer observes his/her own data and implementations where the data is reviewed or analyzed by technical, research, medical, or other oversight personnel. A case for which the wearer would review his/her own data may include, for example, an instrumented appliance which acts as an orthodontic realignment appliance. The data could indicate to a wearer when he/she should change from one realignment appliance to another in a series of realignment appliances. Another instance could be if the appliance is a sleep monitor. The user could review his/her sleep data similar to existing sleep monitoring devices.

Implementations that may require the data to be reviewed and analyzed by medical personnel are for, for example, sleep apnea appliances. Data collected from an appliance that facilitates a home sleep study could be sent to sleep clinic personnel to review and analyze. An implementation that would require review of data by research personnel could also be the collection of kinematic data during head impacts in sports applications. Team, league, parental, medical, or other oversight personnel could analyze data to determine if an intervention should be administered such as training, further evaluation, medical treatment, removal from participation, or other interventions to improve athlete safety.

In embodiments, the inclusion of a visual interface on the case allows the wearer or technical, research, medical, or other oversight personnel managing the case to know the status of the case and the appliance. For example, an LED or series of LEDs could provide visual feedback using different color lights, sequences of flashing lights, or constant illumination of a color. In an aspect, a solid blue (or other color) light may indicate that data is ready and needs to be uploaded to a central data repository. In another aspect, a flashing blue light would indicate the case is receiving data from the appliance, a flashing green light indicates the appliance is being charged, but data is not being transmitted, a solid green light would indicate the appliance is charged, a solid red light indicates a mechanical integrity test failure, and a flashing red light indicates the case is low on power. These are provided as examples and are not thought to be exhaustive.

The holding cases can be implemented for individuals or as a system for a group of individuals. The holding case has additional utility when included in a system for a group of individuals. This aspect allows each user to handle his/her own appliance and place it into the case as he/she would a traditional appliance and case. This allows the administrator/manager of the system to only handle cases. Implementing a physical barrier between individual intra-oral appliances and the system administrator/manager eliminates the need for the administrator/manager to directly handle each appliance. This prevents the system administrator/manager from being contaminated by saliva or having to wear and change surgical gloves often. It also prevents cross contamination between wearers by eliminating the need for a third party to handle each device.

When smart holding cases are implemented as a system for a group, the intent would be that each individual would handle his/her appliance and place his/her own device in the appropriate case. Furthermore, the appliance and device could be labeled to ensure the appliance was placed in the correct case. However, there are scenarios where an unlabeled appliance would need to be matched with its case. One example is if a group of unlabeled appliances were sanitized in a central container. As they were removed, the appliances would need to be matched with their respective cases. The appliances could have a passive RFID or NFC tag that was paired with the correct case. The case in turn would have an active RFID or NFC antenna in the lid or otherwise in the case. This would allow a system administrator/manager to move the appliance over a series of cases to identify the matching case without having to identify the correct case by trial and error.

Figure 1:
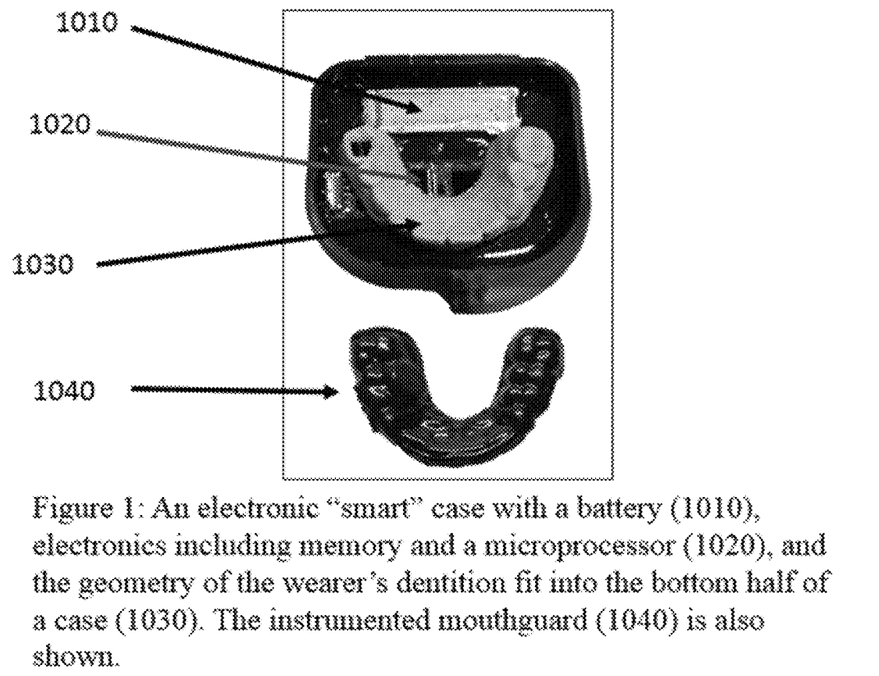
FIG. 1 shows a photo of a possible embodiment of an electronic intra-oral appliance case according to the present invention with a rechargeable battery; electronics circuit board including a microprocessor, memory, antenna for wireless communication, and circuitry for battery charging; a portion of the wearer's dentition (the geometry of the wearer's dentition fit into the bottom half of the case); to receive the instrumented appliance.

Turning now to the figures, FIG. 1 shows an electronic case with a battery 1010, electronics including memory and a microprocessor 1020, and the geometry of the wearer's dentition fit into the bottom half of a case 1030. The instrumented mouthguard appliance 1040 is also shown.

Figure 2:
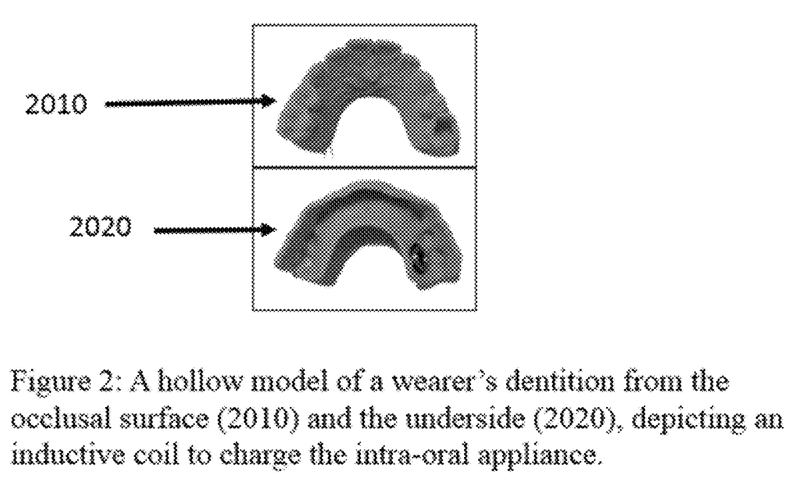
FIG. 2 shows a portion of the dentition according to one possible embodiment of the present invention, which was included in the intra-oral appliance case. The occlusal surface is shown to depict the surface area that interacts with the intra-oral appliance. The underside is also shown to depict how an inductive coil can be placed to align with an inductive coil in the appliance.

FIG. 2 shows a hollow model of a wearer's dentition from the occlusal surface 2010 and the underside 2020, depicting an inductive coil to charge the intra-oral appliance.

Figure 3:
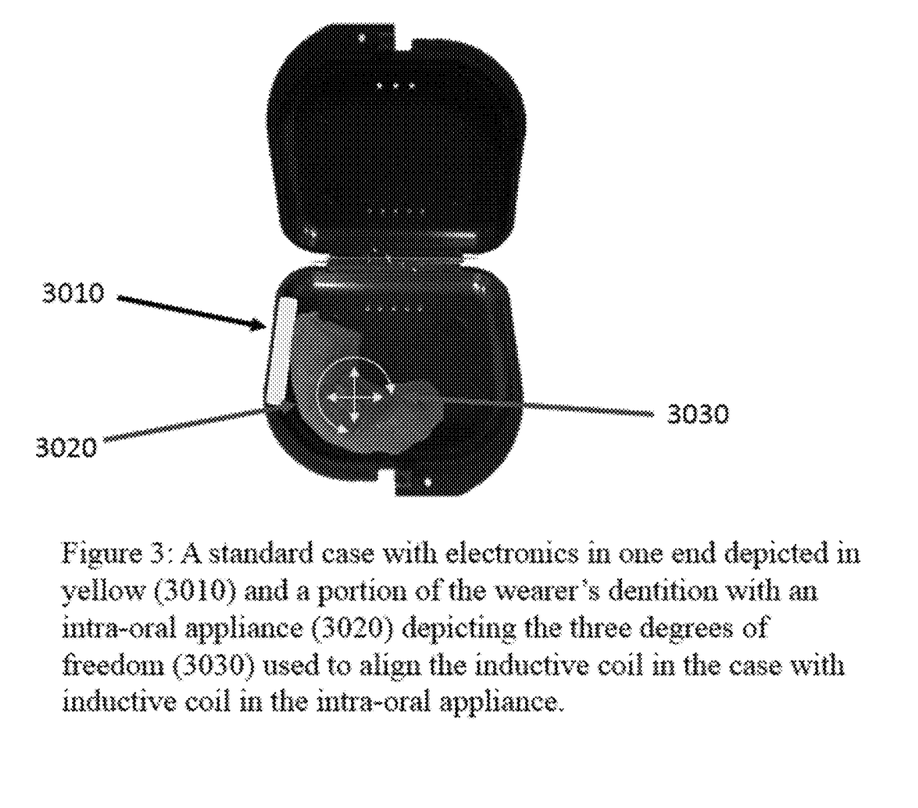
FIG. 3 shows an appliance container according to one possible embodiment of the present invention.

FIG. 3 shows a standard case with electronics in one end depicted in yellow 3010 and a portion of the wearer's dentition with an intra-oral appliance 3020 depicting the three degrees of freedom 3030 used to align the inductive coil in the case with inductive coil in the intra-oral appliance.

Figure 4:
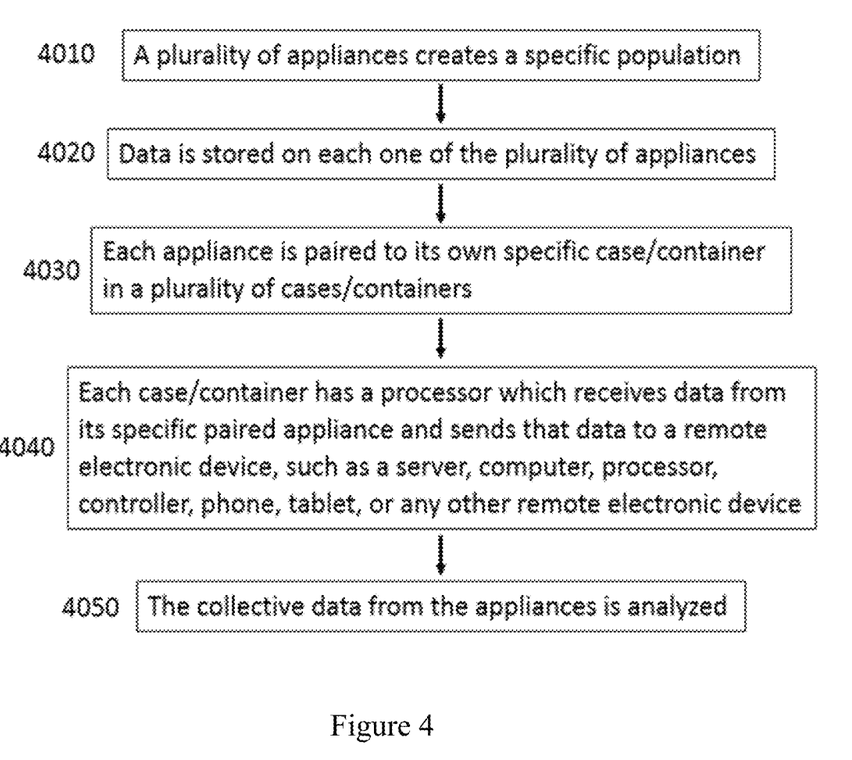
FIG. 4 shows one possible embodiment of the invention taught herein.

FIG. 4 shows a method wherein data from a population of appliances may be shared and analyzed separately or collectively. In one possible embodiment, there are a plurality of appliances constituting a population 4010, such as, for example, an athletics team. Data from each athlete is stored on an appliance used by a particular athlete 4020. Each appliance in the population is paired to a specific container in a plurality of containers 4030. In preferred embodiments, each appliance is pre-paired or paired to a container before use of the appliance. Each container has a processor which receives data from the appliance to which it is paired and sends that data to a remote electronic device, such as another processor, server, computer, or phone 4040. The data from each separate appliance, separately and/or collectively, in situations, is analyzed 4050. The analyzed data may be sent back to an appliance, the plurality of appliances, a computer, a phone, a server, a coach(es), a parent(s), a doctor(s), or anybody or any device supervising the data, appliances, cases, or athletes, by way of example.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A container system for an electronic intra-oral appliance comprising:
   an electronic intra-oral appliance, comprising: one or more sensors, one or more memory units configured to store data received from the one or more sensors, one or more rechargeable batteries, one or more wireless field detect circuits to modify states when being charged, and one or more state machines capable of restricting wireless communication based on charging state;

a container comprising:
  a cavity for holding and/or resting the electronic intra-oral appliance within the cavity,
  one or more circuit boards configured to wirelessly charge the electronic intra-oral appliance, and to enable communication between the electronic intra-oral appliance and the container, or both,
  one or more computer processing units, wherein the one or more computer processing units are configured to receive data from the intra-oral appliance,
  one or more power source configured to charge the electronic intra-oral appliance and/or the container, and
  one or more wired or wireless link configured to transmit data from the one or more computer processing units and/or the electronic intra-oral appliance to one or more remote electronic devices; and
  wherein when the electronic intra-oral appliance is placed in the cavity of the container, wireless communication is enabled to initiate a transfer of data stored on the electronic intra-oral appliance to the one or more computer processing units of the container, the one or more remote electronic devices, or both.

2. The container system of claim 1, wherein the one or more wired or wireless link is also configured to receive data sent from the one or more remote electronic devices.

3. The container system of claim 1, wherein the cavity of the container is open on one or more sides of the container.

4. The container system of claim 1, wherein the cavity of the container is fully enclosed.

5. The container system of claim 1, wherein the one or more remote electronic devices are chosen from one or more of a server, a computer, a computer processing unit, a phone, a television, or a storage medium.

6. The container system of claim 1, wherein the one or more sensors are chosen from an accelerometer, a gyroscope, an oxygen level monitor, a blood oxygen level monitor, a heart rate monitor, a head kinematic monitor, a load cell, a force sensor, a strain gauge, a pressure sensor, a microphone, a blood osmolality sensor, a blood glucose sensor, a PPG sensor, a NIR sensor, ECG, and/or a light sensor.

7. The container system of claim 1, wherein the cavity comprises a full or partial dental geometry of a wearer of the electronic intra-oral appliance and/or a full or partial dental imprint of a wearer of the electronic intra-oral appliance.

8. The container system of claim 7, wherein the full or partial dental geometry of the wearer of the electronic intra-oral appliance and/or the full or partial dental imprint of the wearer of the electronic intra-oral appliance in the cavity of the container is configured to receive the electronic intra-oral appliance.

9. The container system of claim 7, wherein the full or partial dental geometry of the wearer of the electronic intra-oral appliance and/or the full or partial dental imprint of the wearer of the electronic intra-oral appliance in the cavity of the container is configured to align with all or a portion of the electronic intra-oral appliance shape.

10. The container system of claim 1, wherein the one or more power source is chosen from one or more of a battery, an inductive coil, a wired source of electricity, or an electrical outlet.

11. The container system of claim 1, wherein the container comprises a second one or more sensors, one or more gauges, a second one or more circuit boards, a second one or more memory units, one or more storage media, one or more light sources, one or more sound sources, and/or one or more user interfaces.

12. The container system of claim 1, further comprising a visual user display and/or interface.

13. The container system of claim 1, further comprising a graphical user display and/or interface.

14. The container system of claim 1, further comprising an ultra-violet light element to partially or completely sterilize the electronic intra-oral appliance.

15. The container system of claim 1, wherein one or more of the one or more sensors are configured to measure physical and/or electronic contact between the container and the electronic intra-oral appliance.

16. The container system of claim 1, wherein the container comprises software, firmware, hardware, or combinations thereof, configured to determine the mechanical and/or electrical integrity of the connection between the container and the electronic intra-oral appliance.

17. The container system of claim 1, wherein upon insertion of the electronic intra-oral appliance into the container, a mechanical, structural, and/or electrical integrity check of the electronic intra-oral appliance is initiated.

18. The container system of claim 1, wherein upon insertion of the electronic intra-oral appliance into the container, the one or more computer processing units are prompted to record, store, transfer, transmit, send, read, analyze, download, upload, export, import, and/or process data from the electronic intra-oral appliance.

19. The container system of claim 1, wherein one or more of the one or more computer processing units are capable of analyzing the data stored on the electronic intra-oral appliance to determine the mechanical, structural, and/or electrical integrity of the electronic intra-oral appliance.

20. The container system of claim 1, wherein one or more of the one or more computer processing units are capable of analyzing the data stored on the electronic intra-oral appliance to measure and/or monitor human performance or health metrics, head trauma, possibility of injury, blood oxygen level, heart rate, a blood osmolality, blood glucose, elevated risk of injury, and/or head kinematics.

21. The container system of claim 1, wherein the container is one of a plurality of containers, and wherein the plurality of containers are associated with a plurality of electronic intra-oral appliances.

22. The container system of claim 21, wherein each one of the plurality of containers is paired to a single electronic intra-oral appliance of the plurality of electronic intra-oral appliances.

23. The container system of claim 21, wherein the one or more wired or wireless link is capable of transmitting information from the plurality of containers and/or the plurality of electronic intra-oral appliances to a server, a computer, a processor, a storage unit, a computer processing unit, a controller, a phone, and/or a television.

24. A method of collecting data from a plurality of electronic intra-oral appliances comprising:
  providing a plurality of electronic intra-oral appliances;
  storing data on the plurality of electronic intra-oral appliances;

pairing each one of the plurality of electronic intra-oral appliances to one container of a plurality of containers, wherein the plurality of containers each comprises a processor configured to receive and send the data stored on its paired electronic intra-oral appliance;

providing wireless field detection on each of the electronic intra-oral appliances to control wireless communication;

restricting wireless communication of each paired container to occur only when an electronic intra-oral appliance of the plurality of electronic intra-oral appliances is placed in or on its paired container;

each paired container wirelessly transmitting the data stored on the plurality of electronic intra-oral appliances to one or more remote electronic devices; and analyzing the data received from the plurality of electronic intra-oral appliances.

25. The method of claim 24, further comprising identifying one or more of the plurality of electronic intra-oral appliances using a low power wireless protocol.

26. The method of claim 24, further comprising sending information from the one or more remote electronic devices to one or more of the plurality of electronic intra-oral appliances and/or to one or more of the plurality of containers.

* * * * *